United States Patent
Campbell et al.

(10) Patent No.: US 7,279,483 B2
(45) Date of Patent: Oct. 9, 2007

(54) FAMCICLOVIR MONOHYDRATE

(75) Inventors: Kenneth Churchill Campbell, Essex (GB); Michael John Greenway, West Sussex (GB); Stephen Andrew Hancock, Essex (GB)

(73) Assignee: Novartis AG, Basel (CH)

( * ) Notice: Subject to any disclaimer, the term of this patent is extended or adjusted under 35 U.S.C. 154(b) by 241 days.

(21) Appl. No.: 10/980,469

(22) Filed: Nov. 3, 2004

(65) Prior Publication Data

US 2005/0171124 A1 Aug. 4, 2005

Related U.S. Application Data

(63) Continuation of application No. 10/757,905, filed on Jan. 15, 2004, now abandoned, which is a continuation-in-part of application No. 09/735,438, filed on Dec. 13, 2000, now abandoned, which is a continuation of application No. 09/117,823, filed as application No. PCT/EP97/00523 on Feb. 4, 1997, now abandoned.

(30) Foreign Application Priority Data

Feb. 7, 1996 (GB) ................ 9602403.9
Sep. 5, 1996 (GB) ................ 9618494.0

(51) Int. Cl.
*C07D 473/32* (2006.01)
*A61K 31/52* (2006.01)
*A61P 31/22* (2006.01)

(52) U.S. Cl. .................. 514/263.4; 544/277
(58) Field of Classification Search .......... None
See application file for complete search history.

(56) References Cited

U.S. PATENT DOCUMENTS

| | | | |
|---|---|---|---|
| 5,246,937 A | 9/1993 | Harnden et al. | 514/261 |
| 5,250,688 A | 10/1993 | Harnden et al. | 544/277 |
| 2004/0097528 A1* | 5/2004 | Dolitzky et al. | 514/263.4 |
| 2006/0004027 A1* | 1/2006 | Eisen-Nevo et al. | 514/263.35 |

FOREIGN PATENT DOCUMENTS

AU 4 756 085 3/1986

OTHER PUBLICATIONS

Vere Hodge et al. Antimicrob. Agents Chemother. 33 (10): 1765 (1989).*
Harnden, Nucleosides and Nucleotides 9, 499 (1990).*
Bacon et al., "Activity of Penciclovir Against Epstein-Barr Virus", Antimicrobial Agents and Chemotherapy, vol. 39, No. 7, pp. 1599-1602 (1995).
Boyd et al., "Antiherpesvirus Activity of 9-(4Hydroxy-3-Hydroxy-Methylbut-1-yl) Guanine (BRL 39123) in Cell Culture", Antimicrobial Agents and Chemotherapy, vol. 31, No. 8, pp. 1238-1242 (1987).
Neyts et al, "Antiviral Drug Susceptibility of Human Herpesvirus 8", Antimicrobial Agents and Chemotherapy, vol. 41, No. 12, pp. 2754-2756 (1997).
Harnden et al. "Prodrugs of the Selective Antiherpesvirus Agent 9-[4-Hydroxy-3-(hydroxymethyl)but-1-yl]guanine (BRL 39123) with Improved Gastrointestinal Absorption Properties", J. Med. Chem., vol. 32, No. 8, pp. 1738-1743 (1989).
http://www.nursespdr.com/members/database/ndrhtml/famciclovir.html downloaded from the internet Jul. 10, 2003.

* cited by examiner

*Primary Examiner*—Mark L. Berch
(74) *Attorney, Agent, or Firm*—Thomas Savitsky

(57) ABSTRACT

Famciclovir monohydrate and its pharmaceutical use.

3 Claims, No Drawings

FAMCICLOVIR MONOHYDRATE

This is a continuation of application Ser. No. 10/757,905 filed on Jan. 15, 2004, now abandoned which is a continuation-in-part of application Ser. No. 09/735,438 filed on Dec. 13, 2000, now abandoned which is a continuation of application Ser. No. 09/117,823 filed on Dec. 2, 1998, now abandoned which is a National Stage of International Application No. PCT/EP97/00523 filed on Feb. 4, 1997, the entire disclosures of which are hereby incorporated by reference.

FIELD OF INVENTION

This invention relates to a novel form of a pharmaceutical, and having pharmacological activity, to a process for its preparation and to its use as a pharmaceutical.

EP-A-182024 (Beecham Group p.l.c.), Example 2 describes a method of the preparation of famciclovir, a compound which is useful as the oral form of the compound, penciclovir which has antiviral activity against infections caused by herpesviruses, such as herpes simplex type 1, herpes simplex type 2 and varicella zoster virus, and also against Hepatitis B virus. Penciclovir and its antiviral activity is disclosed in Abstract P.V11-5 p. 193 of 'Abstracts of 14th Int. Congress of Microbiology', Manchester, England 7-13 September 1986 (Boyd et. al.).

The form of famciclovir used for formulating into tablets or capsules is the anhydrous form as this form is stable and has good handling qualities for commercial production. In the case of a suspension formulation, however this form of famciclovir has potential disadvantages in terms of crystal growth in solution.

A pure, crystalline hydrate of famciclovir has been discovered, this hydrate having surprisingly improved properties, useful in a suspension formulation.

SUMMARY OF THE INVENTION

Accordingly, the present invention provides famciclovir monohydrate.

DETAILED DESCRIPTION OF THE INVENTION

The hydrate is preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%. One preferred pharmaceutically acceptable form is the crystalline form, including such form in a pharmaceutical composition.

The invention also provides a process for the preparation of a famciclovir monohydrate which process comprises dissolving anhydrous famciclovir in an aqueous medium and allowing the monohydrate to precipitate out from the solution.

The anhydrous famciclovir is preferably dissolved in hot water at a temperature greater than 25 degrees centigrade, usually 50 to 60 degrees centigrade, and the hot solution allowed to cool slowly to 5 degrees centigrade with continuous stirring. The monohydrate crystals are then filtered off and allowed to dry at ambient temperature.

The monohydrate may also be formed by exposing the anhydrous form of famciclovir to an atmosphere containing a high concentration of water vapour.

The invention also provides a pharmaceutical composition comprising famciclovir monohydrate, and a pharmaceutically acceptable carrier. In particular, the invention comprises a pharmaceutical composition in the form of an aqueous suspension for oral administration.

Suspension formulations may contain conventional additives such as suspending agents, for example sorbitol, syrup, methyl cellulose, gelatin, hydroxyethylcellulose, carboxymethylcellulose, aluminum stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; bulking agents such as microcystalline cellulose or silicon dioxide; flow agents such as colloidal silica; preservatives, for example methyl or propyl p-hydroxybenzoate or sorbic acid, and if desired conventional flavouring or colouring agents.

The oral compositions may be prepared by conventional methods.

The invention further provides a method of treatment or prophylaxis of viral infections in mammals, such as humans, which comprises the administration of famciclovir monohydrate.

The amount of famciclovir in the oral dosage form will depend on the viral infection being treated, the type of patient and the frequency of administration. Unit dosages are likely to be 125, 250, 500, 750 mg or 1 g, 1 to 3 times a day.

The invention also provides famciclovir monohydrate for use as an active therapeutic substance, in particular for use in the treatment of viral infections.

The following example illustrates the preparation of famciclovir monohydrate and the following comparison test results illustrate the beneficial use of famciclovir monohydrate in a suspension formation. European Journal of Pharmaceutical Sciences, Vol 4 Suppl., September 1996, S170, abstract P3.029, describes the use of FT-Raman Spectroscopy to characterise the pseudopolymorphic transformation of the anhydrate to the monohydrate, and AAPS 11th Annual Meeting, Seattle, Wash., Oct. 27-31, 1996, Abstract/.PDD 7140, *Pharm. Res.,* 13, S-267, 1996, describes the compaction induced solid state reactivity of the anhydrate.

EXAMPLE 1

Famciclovir (150 g) was dissolved in hot water (approximately 200 ml at 50 to 60 degrees centigrade). The hot solution was allowed to cool slowly to 5 degrees centigrade with continuous stirring for 3 hours. The monohydrate crystals were filtered and then dried by allowing the excess water to evaporate under ambient conditions for approximately 2 days.

The monohydrate of famciclovir was characterised by infra-red spectroscopy, thermal analysis and X-ray diffraction methods. Identification was confirmed by proton nuclear magnetic resonance spectroscopy.

Water was determined at 5.3% (theoretical—5.31%) by coulometric titration. This was confirmed by thermogravimetric analysis of the monohydrate which gave a 5.2% weight loss.

EXAMPLE 2

Famciclovir (70 g) is dissolved in hot water (approximately 100 ml at 50 to 60 degrees centigrade). The hot solution is allowed to cool slowly to 5 degrees centigrade with continuous stirring for 3 hours. The monohydrate crystalsare filtered and then dried by allowing the excess water to evaporate under ambient conditions for approximately 2 days.

Comparison Test Results

An investigation was carried out on monohydrate crystal growth in famciclovir suspension. Two suspensions were prepared using the formulae below and were reconstituted with water.

| Famciclovir Monohydrate Suspension | % Composition | Famciclovir Anhydrate Suspension | % Composition |
|---|---|---|---|
| Famciclovir Monohydrate | 35.20 | Famciclovir Anhydrate granules | 34.36 |
| Hydroxy Propyl Methyl Cellulose | 3.33 | Hydroxy Propyl Methyl Cellulose | 3.33 |
| Xanthan Gum | 3.33 | Xanthan Gum | 3.33 |
| Saccharin | 1.78 | Saccharin | 1.78 |
| Aspartame | 2.67 | Aspartame | 2.67 |
| Colloidal Silica | 1.67 | Colloidal Silica | 1.67 |
| Flavours | 6.93 | Flavours | 6.93 |
| Disodium hydrogen Phosphate dihydrate | 19.56 | Disodium hydrogen Phosphate anhydrate | 15.6 |
| Citric acid monohydrate | 2.7 | Citric acid monohydrate | 2.47 |
| Silicon Dioxide | 22.38 | Silicon Dioxide | 27.41 |

The reconstituted suspension was stored at 25° C. and the crystal growth monitored over a period of one week using microscopy.

The results from visual and photographic examination indicate little or no crystal growth in the monohydrate suspension whilst the crystals in the anhydrate suspension had grown to ten times their original size, making them less pharmaceutically acceptable.

The invention claimed is:

1. A method of treating herpes zoster or herpes simplex in a mammal, which method comprises oral administration to said mammal of an effective amount of a pharmaceutical composition comprising famciclovir monohydrate, and a pharmaceutically acceptable carrier, wherein said pharmaceutical composition is in the form of an aqueous suspension.

2. The method according to claim 1 wherein the monohydrate has a purity of at least 90%.

3. The method according to claim 2 wherein the monohydrate is administered in an amount of 125 mg to 1 gm, one to three times daily.

* * * * *